(12) United States Patent
Mikulski

(10) Patent No.: US 6,290,951 B1
(45) Date of Patent: Sep. 18, 2001

(54) ALTERATION OF THE CELL CYCLE IN VIVO, AND PARTICULARLY FOR INDUCING APOPTOSIS OF TUMOR CELLS

(75) Inventor: Stanislaw M. Mikulski, Essex Fells, NJ (US)

(73) Assignee: Alfacell Corporation, Bloomfield, NJ (US)

( * ) Notice: Subject to any disclaimer, the term of this patent is extended or adjusted under 35 U.S.C. 154(b) by 0 days.

(21) Appl. No.: 09/127,619

(22) Filed: Aug. 1, 1998

(51) Int. Cl.⁷ .............................. C12N 5/00; A61K 38/00
(52) U.S. Cl. .................... 424/94.1; 435/375; 435/376; 435/377; 435/383; 514/18
(58) Field of Search ................................. 435/375, 376, 435/377, 383; 424/94.1; 514/18

(56) References Cited

U.S. PATENT DOCUMENTS 5,559,212 * 9/1996 Ardelt ................................ 530/350

OTHER PUBLICATIONS

Ikebe et al. In J of Cancer. 77(4). pp. 578–585 (Abstract Enclosed), 1998.*
Dietrich et al. Proc Natl Acad Sci 93(20) pp. 10815–10819, 1996*
Shinohara et al. Biochem J. 317(2) pp. 385–388, 1996.*
*Cell Tissue Kinet.*(1990), 23, 237–246.
*Br. J. Cancer*(1992). 66, 304–110.
*International Journal of Oncology*3: 57–64, 1993.
*Proc. Natl. Acad. Sci. USA*vol. 94, pp. 855–860, 1997.
*The Embo Journal,* vol. 13, No. 22, pp. 5433–5441 (1994).
*Leukemia*(1998) 12, 1241–1248.
*International Journal of Oncology*13: 633–644, 1998.
*Advances in Cancer Research (1981)*, 35, 269–335.
*Cell Tissue Kinet.*(1990) , 23, 237–246.

* cited by examiner

Primary Examiner—Leon B. Lankford, Jr.

(57) ABSTRACT

A first substance (such as the peptide aldehydes LLnL and LVP) inhibits the function of intracellular proteasome. A second substance (such as ranpirnase) inhibits intracellular protein synthesis or increases intracellular expression of a cyclin-dependent kinase (CDK) inhibitor. Both substances are administered in such a manner that the effects thereof are coincident. The cell cycle of affected tumor cells is therefore arrested and the cells die of apoptosis.

28 Claims, No Drawings

ALTERATION OF THE CELL CYCLE IN VIVO, AND PARTICULARLY FOR INDUCING APOPTOSIS OF TUMOR CELLS

BACKGROUND OF THE INVENTION

The invention relates to cell biology, and more particularly relates to apoptosis. In its most immediate sense, the invention relates to methods for inducing apoptosis in tumor cells in vivo.

It has long been known that cancerous tumors are created by the unregulated growth of undifferentiated tumor cells. Hence, scientists have long sought therapies that would prevent tumor cells from growing.

To do this, scientists have attempted to disrupt the cell cycle of proliferating HL-60 tumor cells by treating them with N-acetyl-leucinyl-leucinyl-norleucinal (LLnL), a peptide aldehyde known to inhibit the function of proteasome. This arrested the HL-60 cells in the G1 phase of the cell cycle, and in turn prevented them from entering the S phase. When such cells were thus prevented from progressing to subsequent stages of the cell cycle, they died (which is a phenomenon known as programmed cell death, or apoptosis).

However, such experiments focus narrowly upon only one aspect of the cell cycle, namely, inhibiting the function of proteasome (which has been shown to be necessary to normal cell-cycle progression). In fact, progression of cells along the cell cycle comes about as a result of a most complex balancing mechanism. At any given point in the cell cycle, the cells are subjected to biological mechanisms that tend to progress them along the cell cycle as well as biological mechanisms that tend to retain them in whatever phase of the cell cycle they are presently in. Whether or not a cell actually progresses from e.g. the G1 phase to the S phase or from the S phase to the G2 phase or from G2 to mitosis (M phase) is determined by a balance of biological forces acting on that cell; if the positive influence of e.g. cyclins (which act to stimulate progression in the cell cycle) predominates over the negative influence of e.g. kinase inhibitors (which act to arrest cells in their existing cell cycle phase), then the cells may enter or leave the S phase; if not, they may not.

The invention proceeds from the realization that existing approaches to promoting apoptosis of tumor cells do not utilize such positive and negative influences concurrently. As a result, such approaches are not as effective as they might otherwise be.

In accordance with the invention, therapeutically effective doses of two substances are administered in vivo in such a manner that their effects are concurrent. The first substance arrests the cells in a particular phase of the cell cycle, and the second substance prevents the cells from progressing beyond that phase. In this way, the above-referenced balancing mechanism is used to most effectively prevent tumor cells from growing and to thereby induce apoptosis.

In accordance with preferred embodiments, the first substance inhibits intracellular proteasome function, or inhibits activation of NFkB, or both. (If the function of proteasome within the cell is inhibited, activation of NFkB within the cell will likewise be inhibited. This is because NFkB is a heterodimer that has as one of its components a protein known as p50. Normally, the p50 protein is produced by proteolytic processing of its precursor protein p105, which processing is a function of proteasome. When proteasome function is inhibited, the p50 protein is not produced, and instead of producing an active NFkB heterodimer from p50 protein and another protein known as p65 protein, an inactive heterodimer is produced from p105 protein and p65 protein. Additionally, when proteasome function is inhibited, this prevents proteolytic degradation of the IkB protein, which inhibits the function of NFkB by complexing with it and preventing it from entering the nucleus of the cell. In other words, inhibition of proteasome function also inhibits the function of NFkB by reducing the extent to which an inhibitor of NFkB is destroyed.) Two peptide aldehydes, namely LLnL and N-acetyl-leucinyl-valinyl-phenylalaninal (LVP), are suitable for this.

The phase in which inhibition of intracellular proteasome function arrests the cell cycle may vary. As stated above, in HL-60 cells the arrest occurs in the G1 phase, but in DU-145 human prostate carcinoma cells, the arrest occurs in the G2 phase.

In accordance with the preferred embodiment, the second substance inhibits intracellular protein synthesis, or increases intracellular expression of a cyclin-dependent kinase (CDK) inhibitor such as p27KIP1. Ranpirnase is suitable for this. (Ranpirnase is the USAN-approved generic name of the pharmaceutical that is described and claimed in U.S. Pat. No. 5,559,212 and that is presently known by the registered trademark ONCONASE.)

The above-referenced concurrent effects can be achieved by administering both substances separately (as by injections, oral administrations, or both) as long as the substances are administered in such a manner as to cause their effects to be concurrent. It is believed that the above-referenced concurrent effects can also be achieved by administering both substances simultaneously (as in a mixture or other form containing both).

DETAILED DESCRIPTION OF PREFERRED EMBODIMENTS

In vitro experiments were conducted using five drugs on three cell lines. The drugs were ranpirnase, doxorubicin, LLnL, LVP, and N-acetyl-leucinyl-leucinyl-methioninal (LLM), and the cell lines were DU-145 human prostate carcinoma, A-549 human lung carcinoma, and MDA-MB-231 human breast carcinoma. In vivo experiments were conducted using ranpirnase, doxorubicin and LLnL and the MDA-MB-231 human breast carcinoma cell line in nude mice.

In vitro Materials and Methods: Cell Lines

The DU-145, A-549, and MDA-MB-231 cell lines were purchased from the American Type Culture Collection. The A-549 cells were grown as previously described in *Cell Tissue Kinet* 23:237, 1990. The DU-145 cell line was maintained in Eagle's Minimum Essential Medium supplemented with 10% fetal bovine serum (FBS), 1% glutamine, and 1% Pen-Strep-Fungizone. The cell number of DU-145 cells used in the MTT assay was 10,000 cells/well. The MDA-MB-231 cell line was maintained in Liebovitz's L-15 medium supplemented with 10% FBS, 1% glutamine, and 1% Pen-Strep-Fungizone. The cell number of the MDA-MB-231 cells used in the MTT assay was 10,000 cells/well. All agents were obtained from JRH Bioscience, Lenexa, Kans. The determination of cell number, description of the MTT calorimetric assay, and statistical analyses (including assessments of synergistic interactions) were as previously described in *Cell Tissue Kinet* 23:237, 1990 and Adv Cancer Res 35:269, 1981.

In vitro Drugs

Ranpirnase was dissolved as previously described in *Cell Tissue Kinet* 23:237, 1990. The LLnL, LIM, and N-acetylleucinyl-valinyl-phenylalaninal (LVP) were purchased from Sigma Corporation, St Louis, Mo. All three were dissolved in 100% ethanol to produce a 1 μM stock solution. The stock solution was diluted in growth medium of the cell line being tested to produce the solution that was added to the plates containing the cells for the MTT assay.

In vitro Experimental Results

Ranpirnase and LLnL interact synergistically against the DU-145, A-549, and MDA-MB-231 cell lines (Tables 1 and 2). In the A-549 and DU-145 cell lines, the anti-tumor activity of ranpirnase was also augmented by LVP but not by LLM (Table 3). The activity of ranpirnase against the MDA-MB-231 cell line was only minimally affected by the additional treatment with 25 μM LLM (the mean $ED_{50}$ value was decreased by approximately two-fold (Table 3). These findings are consistent with a previously published report in Proc Natl Acad Sci USA 94:855–860, 1997 that LLM peptide does not significantly inhibit the activity of proteasome.

In MDA-MB-231 cells, ranpirnase interacts synergistically with LLnL at the final concentrations of ranpirnase in the range of 0.1 to 10.0 μg/mL and of LLnL in the range of 5 to 25 μM, and particularly at the LLnL concentrations in the range between 10 and 25 μM. The mean $ED_{50}$ value for ranpirnase decreased from 1.434 μg/mL (ranpirnase alone) to 0.037, 0.022, and 0.001 μg/mL for ranpirnase in combination with LLnL at, respectively, the 10, 15, and 25 μM concentrations of LLnL (Table 2). In addition, the combinations of ranpirnase with 0.1 μg/mL (approximately 0.17 μM) doxorubicin with and without 15 μM LLnL were tested (Table 4). The mean $ED_{50}$ value for ranpirnase when used in combination with doxorubicin was decreased 2.2-fold as compared with the mean $ED_{50}$ value for ranpirnase alone. In these conditions, the addition of doxorubicin did not significantly decrease cell growth or cell viability when the triple combination of ranpirnase plus doxorubicin plus LLnL was compared with ranpirnase plus LLnL without doxorubicin (Table 4).

In A-549 cells, the combination of ranpirnase and LLnL was synergistic at higher concentrations (15 to 35) μM of LLnL (Table 1). Lower concentrations of 10 μM of LLnL with lower concentrations (0.1 to 1.0 μg/mL) of ranpirnase were not synergistic, but the effect of the combination was greater than the effect of ranpirnase alone (Table 2). The mean $ED_{50}$ value for ranpirnase decreased from 3.944 μg/mL (ranpirnase alone) to 1.356, 0.640, 0.060, and less than 0.001 μg/mL for the combinations of ranpirnase with LLnL at, respectively, LLnL concentrations of 10, 15, 25, and 35 μM (Table 2).

In DU-145 cells, ranpirnase was synergistic with LLnL across all the concentrations of ranpirnase and the 10 to 25 μM concentrations of LLnL (Table 1). The respective $ED_{50}$ values for ranpirnase alone and for ranpirnase combined with 10, 15, and 25 μM LLnL, were: 42.276, 1.231, 0.001, and <0.001 μg/mL (Table 2). To test whether the observed anti-tumor activity of the combination resulted from apoptosis, an excess (at the final concentrations of 50 μpM) of Ac-DEVD-cho (N-acetyl-L-aspartyl-L-glutamyl-L-valinyl-L-aspartal) was added to overcome a recognized difficulty of its ability to penetrate plasma membranes. (Ac-DEVD-cho was chosen because it is a known inhibitor of caspases. Caspases are cysteine-proteases that are involved in apoptotic cell death.) Ac-DEVD-cho increased approximately 2- to 3-fold the viability of cells treated with a combination of ranpirnase and 25 μpM LLnL. Under identical conditions, but without ranpirnase, the combination of LLnL and Ac-DEVD-cho increased viability of cells approximately 4-fold as compared with cells treated with LLnL alone (Table 5). This suggests that at least part of the anti-tumor activity observed was a manifestation of apoptotic cell death. Newman-Keuls statistical analyses were performed to establish whether or not the observed differences between the anti-tumor activities of ranpirnase as a single agent and ranpirnase combined with the respective peptide inhibitors were significant (Table 6). As shown, the anti-tumor activity of ranpirnase combined with LLnL proteasome inhibitor was significantly greater than that of each of the agents used as a single agent in all tumor cell lines tested. There was no significant effect of the 25 μM LLM peptide on the growth and viability of the MDA-MB-231 cells when compared with untreated controls, and there was no significant difference between the activity of the combination of ranpirnase and 25 μM LLM peptide and the activity of ranpirnase alone (Table 6).

In flow cytometry studies of DU-145 cells, apoptosis appeared to be concurrent with G2 phase arrest of the cell cycle.

In vivo Experimental Results

In vivo experiments (see Table 7) were carried out on nude mice bearing MDA-MB-231 tumors to compare the activities of ranpirnase and LLnL as single agents with the activity of ranpirnase and LLnL together. The dosages of ranpirnase and LLnL were 2.5 mg and 5 mg per kilogram of mouse body weight, respectively.

In the above-referenced experiments, ranpirnase and LLnL were individually administered in vivo intraperitoneally by two immediately successive injections on a twice-weekly schedule for three weeks. Other forms of administration (e.g. using other dose forms, with or without other agents to enhance delivery to an intended location within the body) may also be possible as long as the effects thereof are coincident. Furthermore, although it is presently expected that it will be most advantageous to administer the invention in a single dose form (with or without the addition of one or more other agents to enhance delivery to an intended location within the body) this has not yet been experimentally verified.

Although at least one preferred embodiment of the invention has been described above, this description is not limiting and is only exemplary.

The scope of the invention is defined only by the claims, which follow:

1. A method for inducing apoptosis of tumor cells in vivo, comprising the steps of:
   administering to the patient a therapeutically active dose of a first substance that inhibits intracellular proteasome function; and
   administering to the patient a therapeutically active dose of a second substance that acts to inhibit intracellular protein synthesis,
   said administering steps being carried out in such a manner that the effects thereof are concurrent.

2. The method of claim 1, wherein the first substance is a peptide.

3. The method of claim 2, wherein the first substance is a peptide aldehyde.

4. The method of claim 3, wherein the peptide aldehyde is N-acetyl-leucinyl-leucinyl-norleucinal (LLnL).

5. The method of claim 3, wherein the peptide aldehyde is N-acetyl-leucinyl-valinyl-phenylalaninal (LVP).

6. The method of claim 1, wherein the second substance is a ribonuclease (RNase).

7. The method of claim 6, wherein the RNase is ranpirnase.

8. A method for inducing apoptosis of tumor cells in vivo, comprising the steps of:
   administering to the patient a therapeutically active dose of a first substance that inhibits intracellular activation of NFkB; and
   administering to the patient a therapeutically active dose of a second substance that acts to inhibit intracellular protein synthesis,
   said administering steps being carried out in such a manner that the effects thereof are concurrent.

9. The method of claim 8, wherein the first substance is a peptide.

10. The method of claim 9, wherein the first substance is a peptide aldehyde.

11. The method of claim 10, wherein the peptide aldehyde is N-acetyl-leucinyl-leucinyl-norleucinal (LLnL).

12. The method of claim 10, wherein the peptide aldehyde is N-acetyl-leucinyl-valinyl-phenylalaninal (LVP).

13. The method of claim 8, wherein the second substance is a ribonuclease (RNase).

14. The method of claim 13, wherein the RNase is ranpirnase.

15. A method for altering the cell cycle of cells in a living patient, comprising the steps of:
   administering to the patient a therapeutically active dose of a first substance that inhibits intracellular proteasome function; and
   administering to the patient a therapeutically active dose of a second substance that increases intracellular expression of a cyclin-dependent kinase (CDK) inhibitor,
   said administering steps being carried out in such a manner that the effects thereof are concurrent.

16. The method of claim 15, wherein the CDK inhibitor is p27KIP1.

17. The method of claim 16, wherein the first substance is a peptide.

18. The method of claim 16, wherein the first substance is a peptide aldehyde.

19. The method of claim 18, wherein the peptide aldehyde is N-acetyl-leucinyl-leucinyl-norleucinal (LLnL).

20. The method of claim 18, wherein the peptide aldehyde is N-acetyl-leucinyl-valinyl-phenylalaninal (LVP).

21. The method of claim 16, wherein the second substance is a ribonuclease (RNase).

22. The method of claim 21, wherein the RNase is ranpirnase.

23. A method for inducing apoptosis of tumor cells in vivo, comprising the steps of
   arresting said cells in the G2 phase of the cell cycle by inhibiting intracellular proteasome function, and
   concurrently preventing said cells from progressing beyond said G2 phase of the cell cycle by increasing intracellular expression of a cyclin-dependent kinase inhibitor.

24. A method for inducing apoptosis of tumor cells in vivo, comprising the steps of:
   administering to a living patient a therapeutically active dose of a peptide that inhibits intracellular proteasome function; and
   administering to the patient a therapeutically active dose of a different substance that inhibits intracellular protein synthesis,
   said administering steps being carried out in such a manner that the effects thereof are concurrent.

25. A method for inducing apoptosis of tumor cells in vivo, comprising the steps of:
   administering to a living patient a therapeutically active dose of a peptide that inhibits intracellular proteasome function; and
   administering to the patient a therapeutically active dose of a different substance that increases intracellular expression of a cyclin-dependent kinase (CDK) inhibitor,
   said administering steps being carried out in such a manner that the effects thereof are concurrent.

26. The method of claim 24 or 25, wherein the peptide is N-acetyl-leucinyl-leucinyl-norleucinal (LLnL) or N-acetyl-leucinyl-valinyl-phenylalaninal (LVP), and wherein the different substance is a ribonuclease (RNase).

27. A method for inducing apoptosis of tumor cells in vivo, comprising the steps of:
   administering to a living patient a therapeutically active dose of a peptide selected from a group consisting of N-acetyl-leucinyl-leucinyl-norleucinal (LLnL) and N-acetyl-leucinyl-valinyl-phenylalaninal (LVP); and
   administering to the patient a therapeutically active dose of ranpirnase,
   said administering steps being carried out in such a manner that the effects thereof are concurrent.

28. The method of claim 27, wherein said administering steps are carried out by intravenously injecting ranpirnase and the selected peptide.

* * * * *